US008743362B2

(12) United States Patent
Gono (10) Patent No.: US 8,743,362 B2
(45) Date of Patent: Jun. 3, 2014

(54) OPTICAL MEASUREMENT APPARATUS AND OPTICAL MEASUREMENT SYSTEM (75) Inventor: Kazuhiro Gono, Sagamihara (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/460,209

(22) Filed: Apr. 30, 2012

(65) Prior Publication Data

US 2013/0016351 A1     Jan. 17, 2013

Related U.S. Application Data (63) Continuation of application No. PCT/JP2011/074566, filed on Oct. 25, 2011.

(60) Provisional application No. 61/408,213, filed on Oct. 29, 2011.

(51) Int. Cl.
*G01J 3/46* (2006.01)
*A61B 1/00* (2006.01)
*A61B 5/00* (2006.01)

(52) U.S. Cl.
CPC ......... *A61B 1/00006* (2013.01); *A61B 1/00057* (2013.01); *A61B 5/0075* (2013.01); *A61B 5/0084* (2013.01); *A61B 5/0071* (2013.01)
USPC ........... 356/402; 600/316; 600/322; 600/477; 600/479

(58) Field of Classification Search
CPC ........... A61B 1/00006; A61B 1/00057; A61B 560/0233; A61B 5/0075; A61B 5/0084; A61B 5/0071
USPC ............. 600/316, 322, 477, 479; 324/750.02; 356/402
See application file for complete search history.

(56) References Cited

U.S. PATENT DOCUMENTS 6,203,492 B1   3/2001 Davis
2002/0039022 A1*  4/2002 Yamamoto ............... 324/158.1
(Continued)

FOREIGN PATENT DOCUMENTS

JP     A-61-96891     5/1986
JP     A-10-276975    10/1998
(Continued)

OTHER PUBLICATIONS

Nov. 29, 2011 International Search Report issued in PCT/JP2011/074566.

(Continued)

*Primary Examiner* — Baisakhi Roy
(74) *Attorney, Agent, or Firm* — Oliff PLC (57) ABSTRACT An optical measurement apparatus, to which a base end portion of a measurement probe introduced into a subject is connected so that scattering light from the subject through the measurement probe can be measured, includes: calibration member serving as an irradiation target of illumination light when a calibration process is performed for the measurement probe using the illumination light from the measurement probe; an insertion portion where a leading end of the measurement probe can be inserted; a housing portion that communicates with the insertion portion and accommodates the calibration member movably along a penetration direction of the insertion portion; a detection unit that detects insertion of the measurement probe when the calibration member reaches a predetermined position in the housing portion by the insertion of the measurement probe through the insertion portion; and a control unit that performs control for initiating the calibration process when the detection unit detects the insertion of the measurement probe.

7 Claims, 7 Drawing Sheets

(56) References Cited

U.S. PATENT DOCUMENTS

2011/0313296 A9 * 12/2011 Johnson et al. ............... 600/477
2012/0283530 A1 * 11/2012 Maynard et al. .............. 600/316

FOREIGN PATENT DOCUMENTS

| | | |
|---|---|---|
| JP | A-2004-49708 | 2/2004 |
| JP | A-2004-344363 | 12/2004 |
| JP | A-2005-237641 | 9/2005 |
| JP | A-2005-261636 | 9/2005 |
| JP | A-2006-94992 | 4/2006 |
| JP | A-2006-325690 | 12/2006 |
| JP | A-2008-29751 | 2/2008 |
| JP | A-2008-55130 | 3/2008 |

OTHER PUBLICATIONS

European Search Report dated Jan. 18, 2013 for European Patent Application No. 11836282.1.

* cited by examiner

OPTICAL MEASUREMENT APPARATUS AND OPTICAL MEASUREMENT SYSTEM

CROSS-REFERENCE TO RELATED APPLICATIONS

This application is a continuation of PCT international application Ser. No. PCT/JP2011/074566 filed on Oct. 25, 2011 which designates the United States, incorporated herein by reference, and which claims the benefit of priority from U.S. Provisional Patent Application No. 61/408,213, filed on Oct. 29, 2010, incorporated herein by reference.

BACKGROUND OF THE INVENTION

1. Field of the Invention

The present invention relates to an optical measurement apparatus and an optical measurement system for irradiating illumination light onto body tissue and estimating properties of the body tissue based on a measurement value of detection light reflected or scattered from body tissue.

2. Description of the Related Art

In the related art, there is known a living body optical measurement system for irradiating illumination light onto body tissue and estimating properties of body tissue based on a measurement value of detection light reflected or scattered from the body tissue. Such a living body optical measurement system is used in combination with an endoscope for observing internal organs such as digestive organs.

Incidentally, in the living body optical measurement system described above, it is necessary to perform a calibration process for adjusting white balance before starting the measurement of body tissue in order to guarantee analysis accuracy of the analysis result. In this regard, there is known a technique of irradiating illumination light onto an optical member that reflects light, receiving the reflected light using a photo detector, computing a measurement value, and performing a calibration process based on the computed measurement value and a predetermined reference value before starting the measurement (for example, Japanese Laid-open Patent Publication No. 2006-94992).

SUMMARY OF THE INVENTION

An optical measurement apparatus according to an aspect of the present invention, to which a base end portion of a measurement probe introduced into a subject is connected so that scattering light from the subject through the measurement probe can be measured, includes: a calibration member serving as an irradiation target of illumination light when a calibration process is performed for the measurement probe using the illumination light from the measurement probe; an insertion portion where a leading end of the measurement probe can be inserted; a housing portion that communicates with the insertion portion and accommodates the calibration member movably along a penetration direction of the insertion portion; a detection unit that detects insertion of the measurement probe when the calibration member reaches a predetermined position in the housing portion by the insertion of the measurement probe through the insertion portion; and a control unit that performs control for initiating the calibration process when the detection unit detects the insertion of the measurement probe.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, an optical measurement system, an optical measurement apparatus, and a calibration module according to exemplary embodiments of the invention (hereinafter, referred to as an "embodiment") will be described with reference to the accompanying drawings. The invention is not limited to the embodiments described below. In the description of drawings, like reference numerals denote like elements. It should be noted that the drawings are schematic, and the relation between the thickness and the width of each element or the ratio of each element may be different from actual one. The relation of dimensions or the ratio of each element may be different between each of the drawings.

First Embodiment

Figure 1:
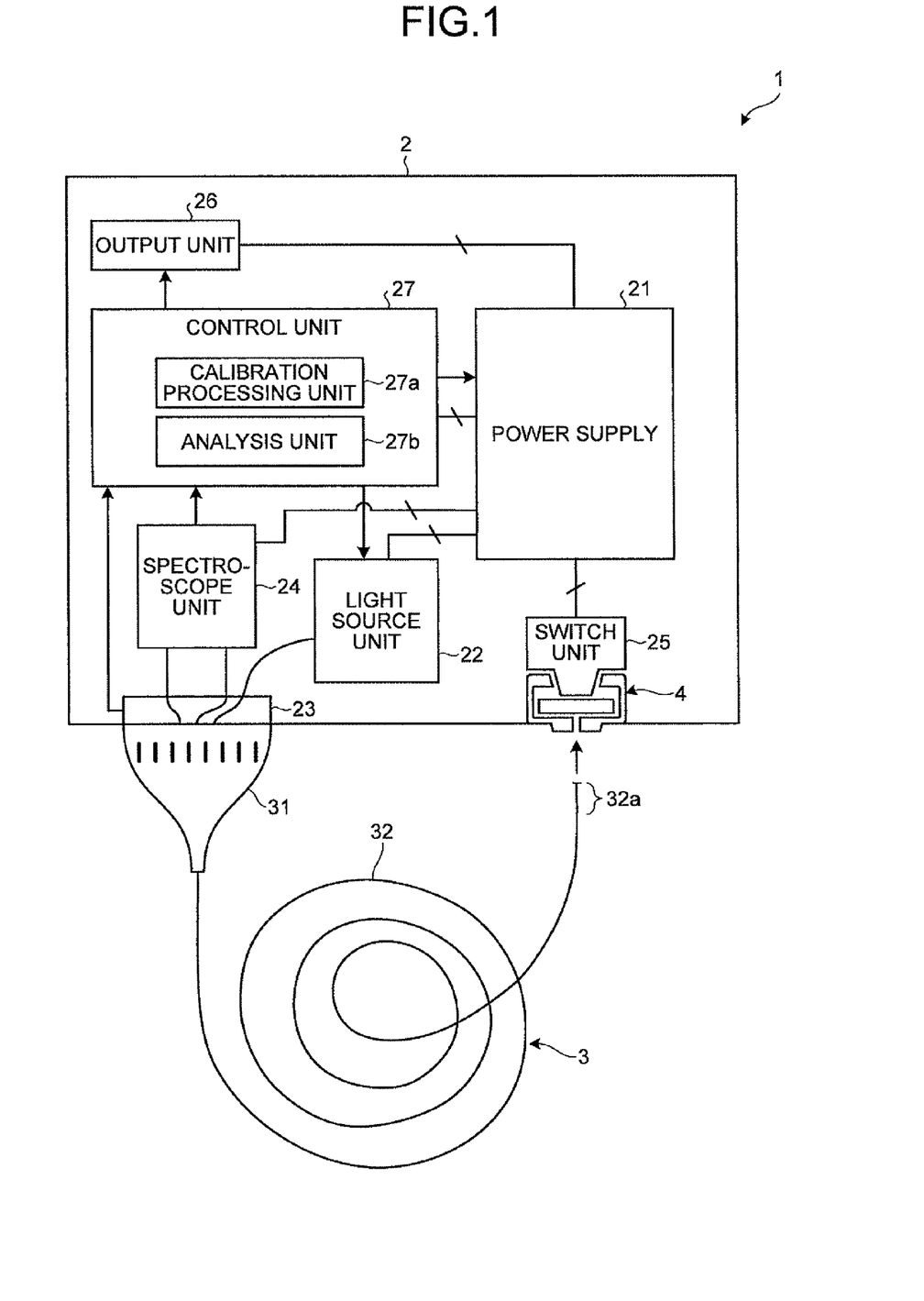
FIG. 1 is a schematic diagram illustrating a schematic configuration of an optical measurement system according to a first embodiment of the invention.

FIG. 1 is a schematic diagram illustrating a schematic configuration of an optical measurement system according to a first embodiment of the invention. As illustrated in FIG. 1, an optical measurement system 1 includes: an optical measurement apparatus 2 that performs optical measurement by irradiating illumination light onto body tissue and receiving reflection light and/or scattering light (hereinafter, referred to as "detection light") of the illumination light reflected or scattered by the body tissue; a measurement probe 3 introduced into a subject; and a calibration module 4 used in the calibration process of the optical measurement system 1.

The optical measurement apparatus 2 includes: a power supply 21 that supplies power to each unit of the optical measurement apparatus 2; a light source unit 22 that emits illumination light onto a target (hereinafter, referred to as a "measurement target") such as body tissue; a connector 23 for connecting the measurement probe 3; a spectroscope unit 24 that receives detection light incident from the measurement probe 3 and measures detection light; a switch unit 25 that activates the power supply 21; an output unit 26 that outputs various information; and a control unit 27 that controls the operation of the optical measurement apparatus 2.

The light source unit 22 includes an incoherent light source such as white LED (light emitting diode) or a xenon lamp and one or more lenses as necessary. The light source unit 22 emits the illumination light onto the measurement target through the connector 23 and the measurement probe 3.

The connector 23 is used for the connection of the measurement probe 3. The connector 23 emits the illumination light emitted from the light source unit 22 to the measurement probe 3 and emits the detection light incident through the measurement probe 3 to the spectroscope unit 24. The connector 23 outputs, to the control unit 27, information regarding whether or not the measurement probe 3 is connected. This information is, for example, a detection signal obtained by detecting the measurement probe 3.

The spectroscope unit 24 includes a spectroscope. The spectroscope unit 24 receives the detection light incident through the connector 23 and the measurement probe 3 and measures spectral components or the like of the received detection light. The spectroscope unit 24 outputs the measurement result obtained by measuring the detection light to the control unit 27.

The switch unit 25 includes a push-type switch and the like. The switch unit 25 activates the power supply 21 in response to a manipulation force applied from an external side.

The output unit 26 includes a display, a loudspeaker, a motor, and the like. The output unit 26 outputs the measurement result of the measurement target or various types of information regarding the optical measurement apparatus 2. Specifically, the output unit 26 outputs various types of information regarding the optical measurement apparatus 2 using sound, images, vibration, or the like.

The control unit 27 includes a CPU (central processing unit) and semiconductor memory such as RAM (random access memory). The control unit 27 transmits instructions or data for each unit of the optical measurement apparatus 2 and the like to collectively control the operation of the optical measurement apparatus 2. The control unit 27 includes a calibration processing unit 27a and an analysis unit 27b. The calibration processing unit 27a initiates a calibration process in the optical measurement apparatus 2 and the measurement probe 3 using the illumination light irradiated from the leading end of the measurement probe 3 when the power supply 21 is activated. The analysis unit 27b analyzes a composition of the measurement target by analyzing spectral components of the detection light received by the spectroscope unit 24 based on the measurement result output from the spectroscope unit 24.

The measurement probe 3 includes one or more optical fibers. For example, the measurement probe 3 includes an illumination fiber for emitting illumination light to the measurement target and a plurality of detection fibers where the detection light reflected or scattered by the measurement target is incident at different angles. The measurement probe 3 includes a base end portion 31 and a flexible portion 32. The base end portion 31 is detachably connected to the connector 23 of the optical measurement apparatus 2. The flexible portion 32 has flexibility. The flexible portion 32 transmits the illumination light emitted from the light source unit 22 to a leading end portion 32a including a leading end where the end face of the optical fiber is exposed and transmits, to the spectroscope unit 24, the detection light incident through the leading end portion 32a.

Figure 2:
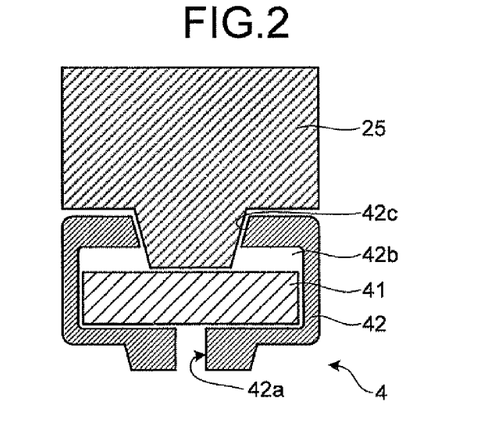
FIG. 2 is a cross-sectional view schematically illustrating cross sections of a switch unit and a calibration module according to the first embodiment of the invention.

FIG. 2 is a cross-sectional view schematically illustrating cross sections of the switch unit 25 and the calibration module 4. As illustrated in FIG. 2, the calibration module 4 includes a calibration member 41 and a casing member 42.

The calibration member 41 includes a standard member having a disc shape. Here, the standard member refers to a member having a white plate or surface having high reflectance for the illumination light. The calibration member 41 serves as an irradiation target of the illumination light irradiated from the leading end portion 32a of the measurement probe 3 when the calibration process is performed in the optical measurement system 1.

The casing member 42 includes an elastic member such as rubber having a cylindrical shape. The casing member 42 includes an insertion portion 42a where a leading end portion 32a of the measurement probe 3 can be inserted, a housing portion 42b communicating with the insertion portion 42a to accommodate the calibration member 41 movably along a penetration direction of the insertion portion 42a, and an opening 42c communicating with the housing portion 42b to hold at least a part of the switch unit 25 where a manipulation force is applied. The casing member 42 is arranged relative to the switch unit 25 such that the manipulation force is applied to the switch unit 25 when the calibration member 41 reaches a predetermined position in the housing portion 42b by inserting the measurement probe 3 from the insertion portion 42a.

An outline of the manipulation sequence of the optical measurement system 1 having the aforementioned configuration will be described. First, a user connects the base end portion 31 of the measurement probe 3 to the connector 23 of the optical measurement apparatus 2.

Figure 3:
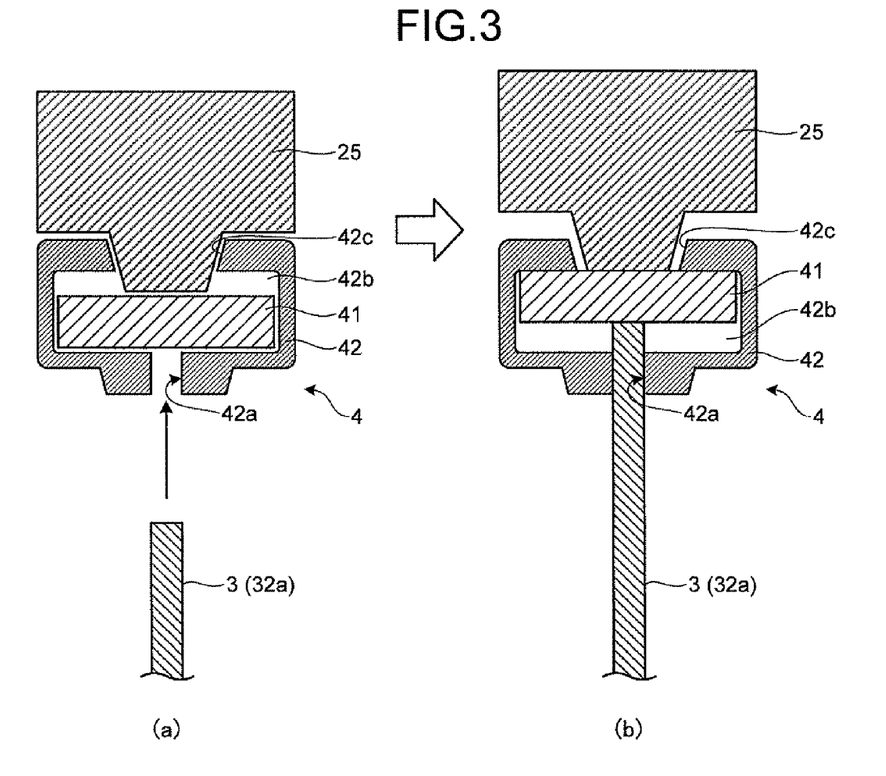
FIG. 3 is a diagram illustrating operations of the switch unit and the calibration module according to the first embodiment of the invention.

Subsequently, a user pressedly inserts the leading end portion 32a of the measurement probe 3 into the insertion portion 42a of the calibration module 4 until the insertion of the measurement probe 3 stops. In this case, as illustrated in FIG. 3, the calibration member 41 presses the switch unit 25 by moving toward the opening 42c side in contact with the leading end portion 32a of the measurement probe 3 (FIG. 3(a) →FIG. 3(b)). As a result, the power supply 21 of the optical measurement apparatus 2 is activated.

Then, the calibration processing unit 27a emits the illumination light to the calibration member 41 by driving the light source unit 22.

Subsequently, the spectroscope unit 24 receives the detection light incident through the leading end portion 32a of the measurement probe 3 and outputs the measurement value of the detection light to the control unit 27. Here, the measurement value includes spectral components of the detection light and the like.

Then, the control unit 27 executes the calibration process of the optical measurement system 1 based on the measurement value output from the spectroscope unit 24 and a predetermined reference value. When this calibration process is executed, the control unit 27 may cause the output unit 26 to output information indicating that the optical measurement system 1 is abnormal when the measurement value output from the spectroscope unit 24 is smaller than a predetermined threshold value. As a result, a user can recognize that the optical measurement apparatus 2 or the measurement probe 3 is abnormal.

Subsequently, the calibration processing unit 27a outputs the information indicating that the calibration process of the optical measurement system 1 is terminated to the output unit 26. As a result, a user can recognize that the calibration process in the optical measurement system 1 is terminated.

Then, a user extracts the leading end portion 32a of the measurement probe 3 from the insertion portion 42a of the calibration module 4 and initiates main measurement using the optical measurement system 1. Specifically, a user introduces the measurement probe 3 into a subject through a treatment tool insertion portion (channel) of the endoscope device and initiates the main measurement. As the main measurement is initiated, the control unit 27 causes the output unit 26 to output the measurement result of body tissue. As a result, a user diagnoses whether or not there is diseased tissue.

After the main measurement is terminated, a user releases connection between the measurement probe 3 and the optical measurement apparatus 2 by extracting the base end portion 31 of the measurement probe 3 from the connector 23 of the optical measurement apparatus 2. In this case, the connector 23 stops output of the detection signal of the measurement probe 3. The control unit 27 switches the power supply 21 of the optical measurement apparatus 2 from the on-state to the off-state when the detection signal is not received from the connector 23. As a result, a series of manipulation processes using the optical measurement system 1 is terminated.

In the first embodiment described above, the power supply 21 of the optical measurement apparatus 2 is activated by inserting the leading end portion 32a of the measurement probe 3 into the insertion portion 42a of the calibration module 4, and the calibration process of the optical measurement apparatus 2 and the measurement probe 3 is executed in synchronization with activation of the power supply 21. Therefore, it is possible to reliably execute the calibration process of the optical measurement system 1 before the measurement of the measurement target is performed. As a result, it is possible to reliably prevent a user from forgetting to execute the calibration process.

Second Embodiment

Figure 4:
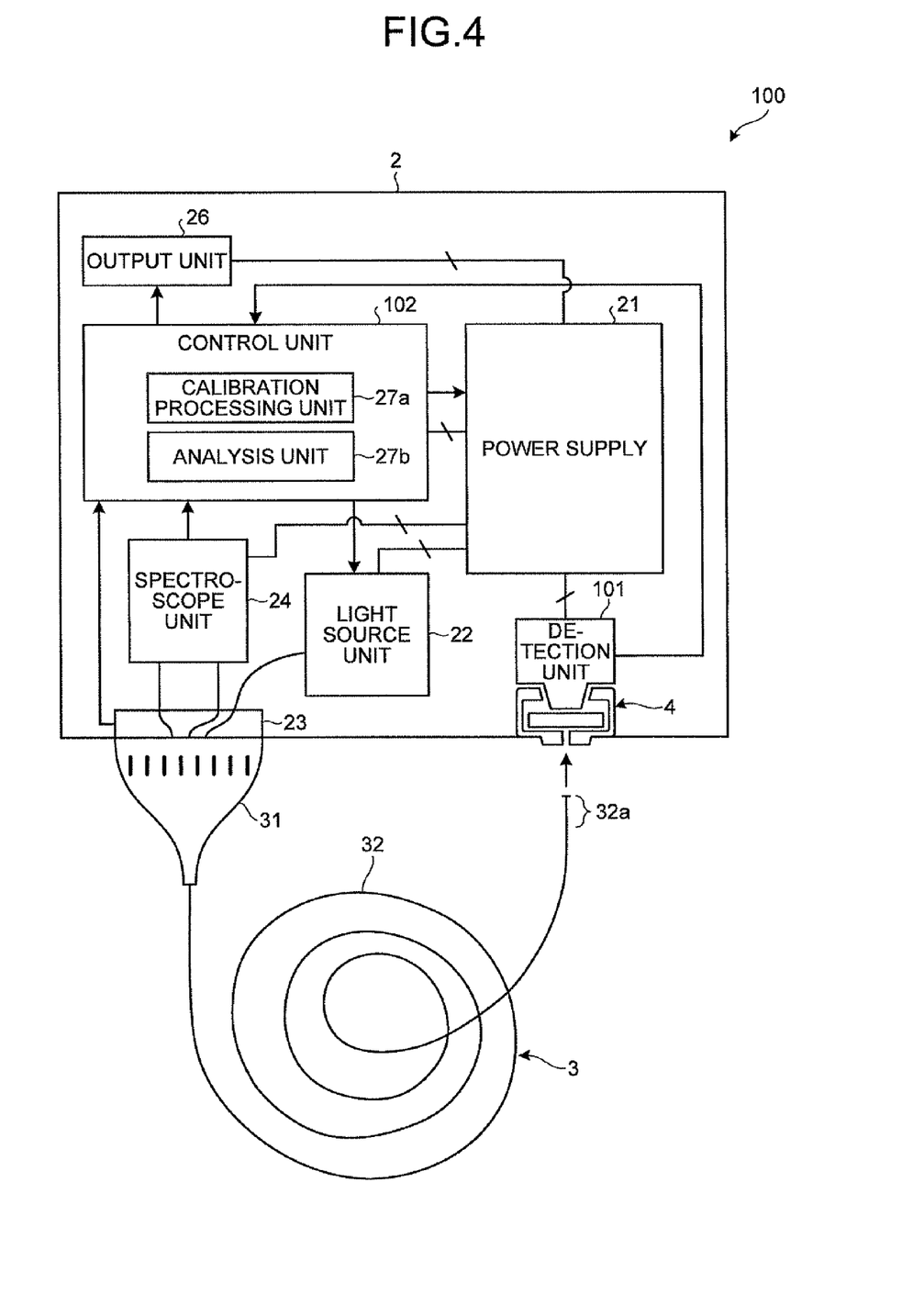
FIG. 4 is a schematic diagram illustrating a schematic configuration of an optical measurement system according to a second embodiment of the invention.

Next, a second embodiment of the invention will be described. FIG. 4 is a schematic diagram illustrating a schematic configuration of an optical measurement system 100 according to the second embodiment. In FIG. 4, like reference numerals denote like elements as in the configuration of the optical measurement system 1 described above in conjunction with the first embodiment, and description thereof will not be repeated.

As illustrated in FIG. 4, the optical measurement system 100 includes a detection unit 101 and a control unit 102.

The detection unit 101 includes a sensitivity sensor, a pressure sensor, or the like. The detection unit 101 determines whether or not the measurement probe 3 is inserted into the calibration module 4 while the power supply 21 of the optical measurement apparatus 2 is activated. Specifically, the calibration member 41 moves toward the opening 42c side when a user inserts the measurement probe 3 into the calibration module 4, and the detection unit 101 detects that the measurement probe 3 is inserted when the calibration member 41 makes contact with the leading end portion of the detection unit 101 in response to this movement and outputs, to the control unit 102, the detection signal indicating this detection.

The control unit 102 drives the light source unit 22 to irradiate illumination light onto the calibration member 41 through the connector 23 and the measurement probe 3 when the detection unit 101 detects insertion of the measurement probe 3 while the power supply 21 of the optical measurement apparatus 2 is activated. Then, the control unit 102 executes the calibration process of the optical measurement system 100 based on the measurement value of the detection light received by the spectroscope unit 24 and a predetermined reference value and then, performs control to switch from a standby mode to a main measurement mode in which the optical measurement can be made for the measurement target.

Here, the standby mode refers to a state that the power supply 21 of the optical measurement apparatus 2 is activated, and activation of the each unit is terminated. In addition, the main measurement mode refers to a state that the control unit 102 can cause the output unit 26 to output the analysis result obtained by analyzing the measurement result of the detection light from the spectroscope unit 24 after the light source unit 22 irradiates illumination light onto the measurement target, and the spectroscope unit 24 receives and measures the detection light incident through the measurement probe 3 and the connector 23.

Figure 5:
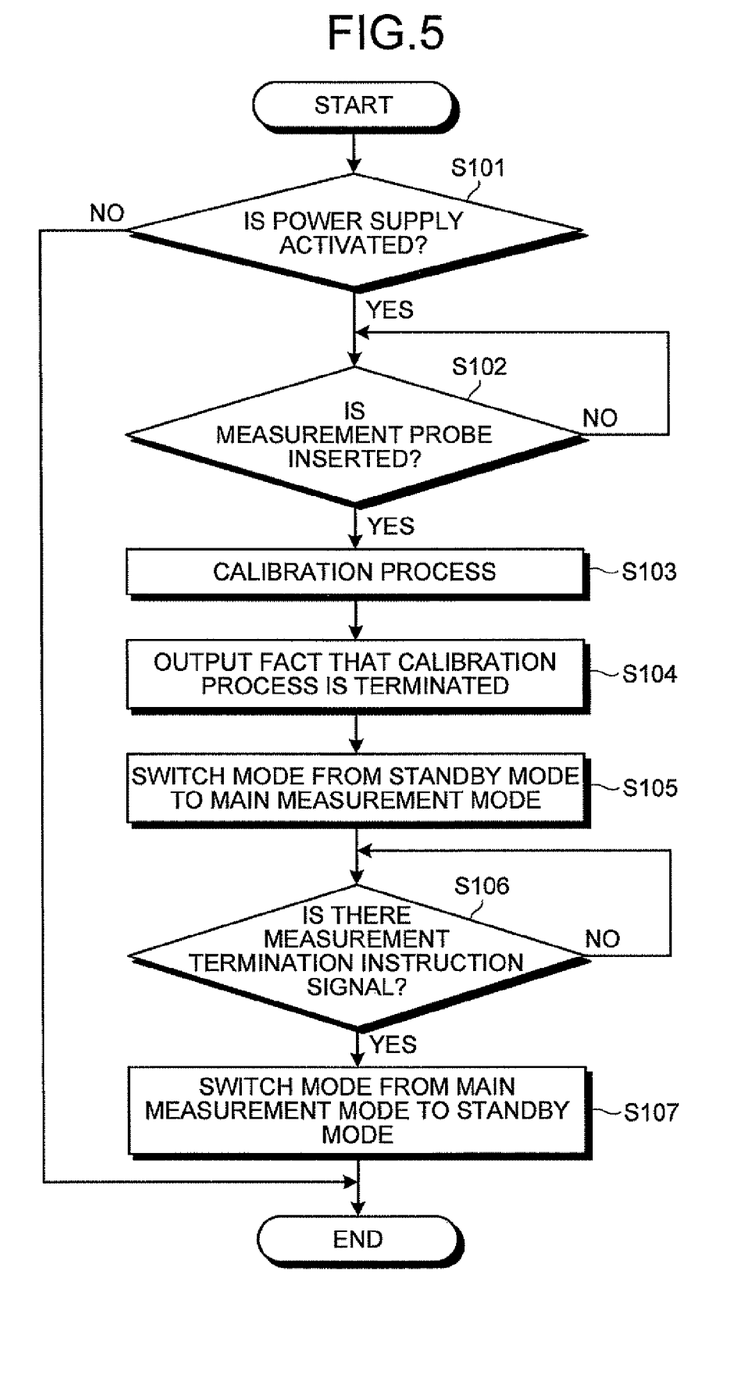
FIG. 5 is a flowchart illustrating an outline of the process in the optical measurement system according to the second embodiment of the invention.

Next, a process performed by the optical measurement system 100 according to the second embodiment will be described. FIG. 5 is a flowchart illustrating an outline of the process performed by the optical measurement system 100.

As illustrated in FIG. 5, first, the control unit 102 determines whether or not the power supply 21 of the optical measurement apparatus 2 is activated (step S101). If the power supply 21 of the optical measurement apparatus 2 is activated (YES in step S101), the optical measurement system 100 advances to step S102 described below. Meanwhile, if the power supply 21 of the optical measurement apparatus 2 is not activated (NO in step S101), the optical measurement system 100 ends this process.

Subsequently, the control unit 102 determines whether or not the detection unit 101 detects insertion of the measurement probe 3 (step S102). If the detection unit 101 does not detect insertion of the measurement probe 3 (NO in step S102), the control unit 102 repeats this determination. Conversely, if the detection unit 101 detects insertion of the measurement probe 3 (YES in step S102), the calibration processing unit 27a executes the calibration process in the optical measurement system 100 (step S103).

After the calibration process in the calibration processing unit 27a is terminated, the control unit 102 causes the output unit 26 to output information indicating that the calibration process is terminated (step S104). In this case, if the measurement value output from the spectroscope unit 24 is smaller than the predetermined threshold value, the calibration processing unit 27a may cause the output unit 26 to output information indicating that the optical measurement system 100 is abnormal.

Subsequently, the control unit 102 switches the mode of the optical measurement system 100 from the standby mode to the main measurement mode (step S105).

Then, the control unit 102 determines whether or not a measurement termination instruction signal is input (step S106). Specifically, the control unit 102 determines whether or not there is a detection signal output from the connector 23. If the measurement termination instruction signal is not input (NO in step S106), the optical measurement system 100 continues to inspect the measurement target. Conversely, if the measurement termination instruction signal is input (YES in step S106), the control unit 102 switches the mode of the optical measurement system 100 from the main measurement mode to the standby mode (step S107), and the optical measurement system 100 terminates the main process.

In the second embodiment described above, even while the power supply 21 of the optical measurement apparatus 2 is activated, the control unit 102 does not switches the optical measurement system 100 from the standby mode to the main measurement mode until a user inserts the measurement probe 3 into the calibration module 4 and executes the calibration process. Therefore, similar to the first embodiment described above, it is possible to reliably execute the calibration process of the optical measurement system 100 before the measurement of the measurement target is performed.

In addition, in the second embodiment described above, the calibration process is executed while the power supply 21 of the optical measurement apparatus 2 is activated. Therefore, there is no standby time generated when the power supply of the optical measurement apparatus 2 is turned on such as a standby time elapsing until the control unit 102 and the spectroscope unit 24 are activated. As a result, it is possible to efficiently measure the measurement target using a plurality of measurement probes 3.

Third Embodiment

Figure 6:
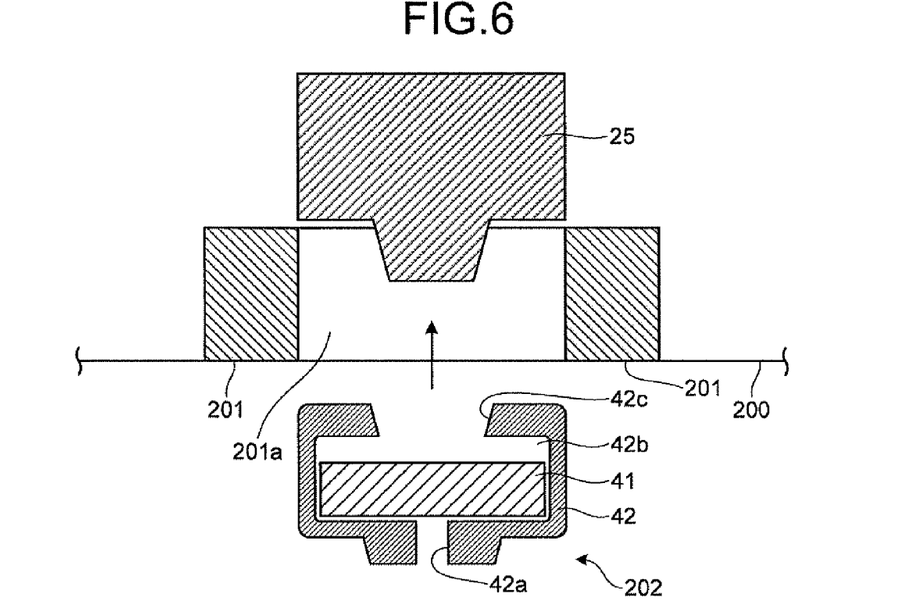
FIG. 6 is a cross-sectional view schematically illustrating cross sections of an optical measurement apparatus, a switch unit, and a calibration module according to a third embodiment of the invention.
Figure 7:
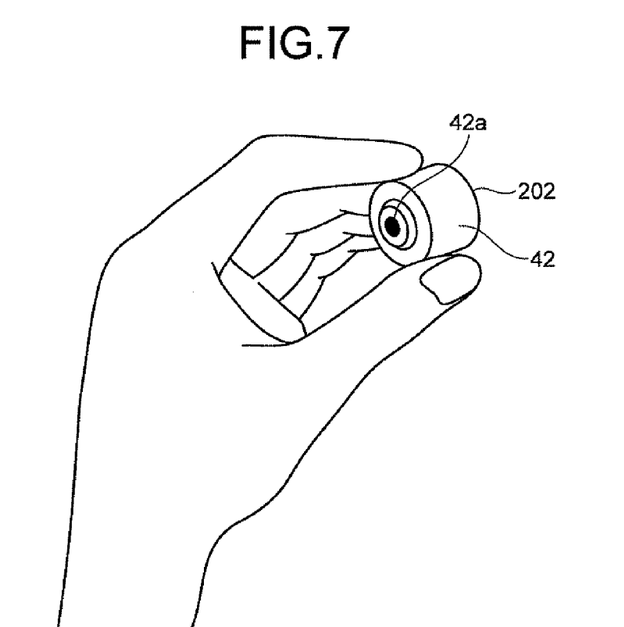
FIG. 7 is a diagram illustrating a use condition of the calibration module according to the third embodiment of the invention.

Next, a third embodiment of the invention will be described. FIG. 6 is a cross-sectional view schematically illustrating cross sections of an optical measurement apparatus, a switch unit, and a calibration module according to the third embodiment. FIG. 7 is a diagram illustrating a use condition of the calibration module according to the third embodiment. In FIGS. 6 and 7, like reference numerals denote like elements as in the configurations of the optical measurement apparatus 2 and the calibration module 4 described above in conjunction with the first embodiment, and description thereof will not be repeated.

As illustrated in FIG. 6, an optical measurement apparatus 200 has a passage for exposing the switch unit 25 and an installation portion 201 where a calibration module 202 can be installed. The installation portion 201 includes an elastic member having a cylindrical shape. The installation portion 201 has an opening 201a for holding the calibration module 202 detachably from the optical measurement apparatus 200.

As illustrated in FIG. 7, the calibration module 202 is detachable from the installation portion 201 of the optical measurement apparatus 200 by a user.

According to the third embodiment described above, since the calibration module 202 is detachably installed in the optical measurement apparatus 200, a user is allowed to easily exchange the calibration module 202 even when the calibration member 41 is deteriorated due to contamination or aging.

In addition, in the third embodiment, a male thread may be formed on the outer circumferential face of the calibration module 202, and a female thread corresponding to the male thread may be formed on the inner circumference face of the opening 201a, so that a user can install the calibration module 202 in the optical measurement apparatus 200 by turning the calibration module 202.

Fourth Embodiment

Figure 8:
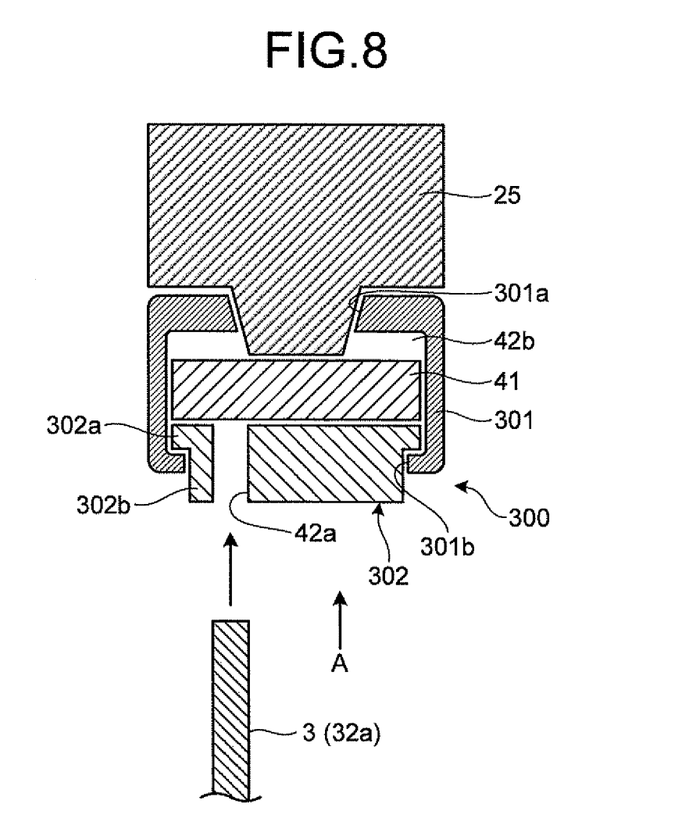
FIG. 8 is a cross-sectional view schematically illustrating a cross section of a calibration module according to a fourth embodiment of the invention.
Figure 9:
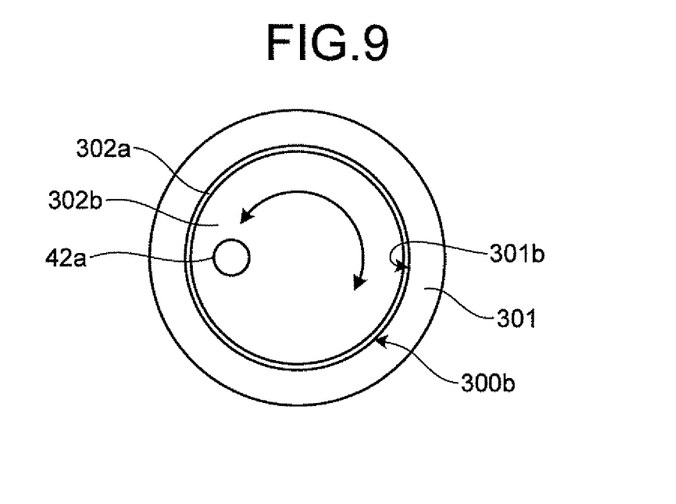
FIG. 9 is a front view as seen from the arrow A of FIG. 8.

Next, a fourth embodiment of the invention will be described. FIG. 8 is a cross-sectional view schematically illustrating a cross section of a calibration module according to the fourth embodiment. FIG. 9 is a front view as seen from the arrow A of FIG. 8. In addition, in FIGS. 8 and 9, like reference numerals denote like elements as in the configurations of the optical measurement system 100 and the calibration module 4 described above in conjunction with the second embodiment, and description thereof will not be repeated.

As illustrated in FIGS. 8 and 9, a calibration module 300 has a casing member 301 and a lid portion 302.

The casing member 301 includes an elastic member having a cylindrical shape. The casing member 301 includes a housing portion 42b for accommodating the calibration member 41, a first opening 301a for holding at least a part of the switch unit 25 where a manipulation force is applied, and a second opening 301b for holding the lid portion 302. The second opening 301b has a hook-shaped cross section so as to prevent the lid portion 302 from getting out of the housing portion 42b.

The lid portion 302 includes an approximately disc-shaped elastic member. In the lid portion 302, an insertion portion 42a where the leading end portion 32a of the measurement probe 3 can be inserted is formed. The lid portion 302 has a large diameter portion 302a and a small diameter portion 302b. The diameter of the large diameter portion 302a is slightly smaller than the diameter of the housing portion 42b and is larger than the diameter of the second opening 301b. As a result, it is possible to prevent the large diameter portion 302a from getting out of the housing portion 42b. The diameter of the small diameter portion 302b is slightly smaller than the diameter of the large diameter portion 302a and is smaller than the second opening 301b.

In the calibration module 300 having the aforementioned configuration, a user can turn the lid portion 302 in a desired direction relative to the casing member 301. Therefore, the lid portion 302 can be used to relatively change a positional relation between the insertion portion 42a and the calibration member 41.

According to the fourth embodiment described above, the lid portion 302 can be used to relatively change the positional relation between the insertion portion 42a and the calibration member 41. Therefore, the calibration process can be executed in a different position of the calibration member 41 whenever the measurement probe 3 is inserted into the calibration module 300. As a result, it is possible to lengthen the lifetime of the calibration module 300 and perform the calibration process in a larger number of times.

Although a user turns the lid portion 302 in the fourth embodiment, for example, the calibration member 41 may be automatically turned at a predetermined angle whenever the measurement probe 3 is inserted into the insertion portion 42a.

Fifth Embodiment

Figure 10:
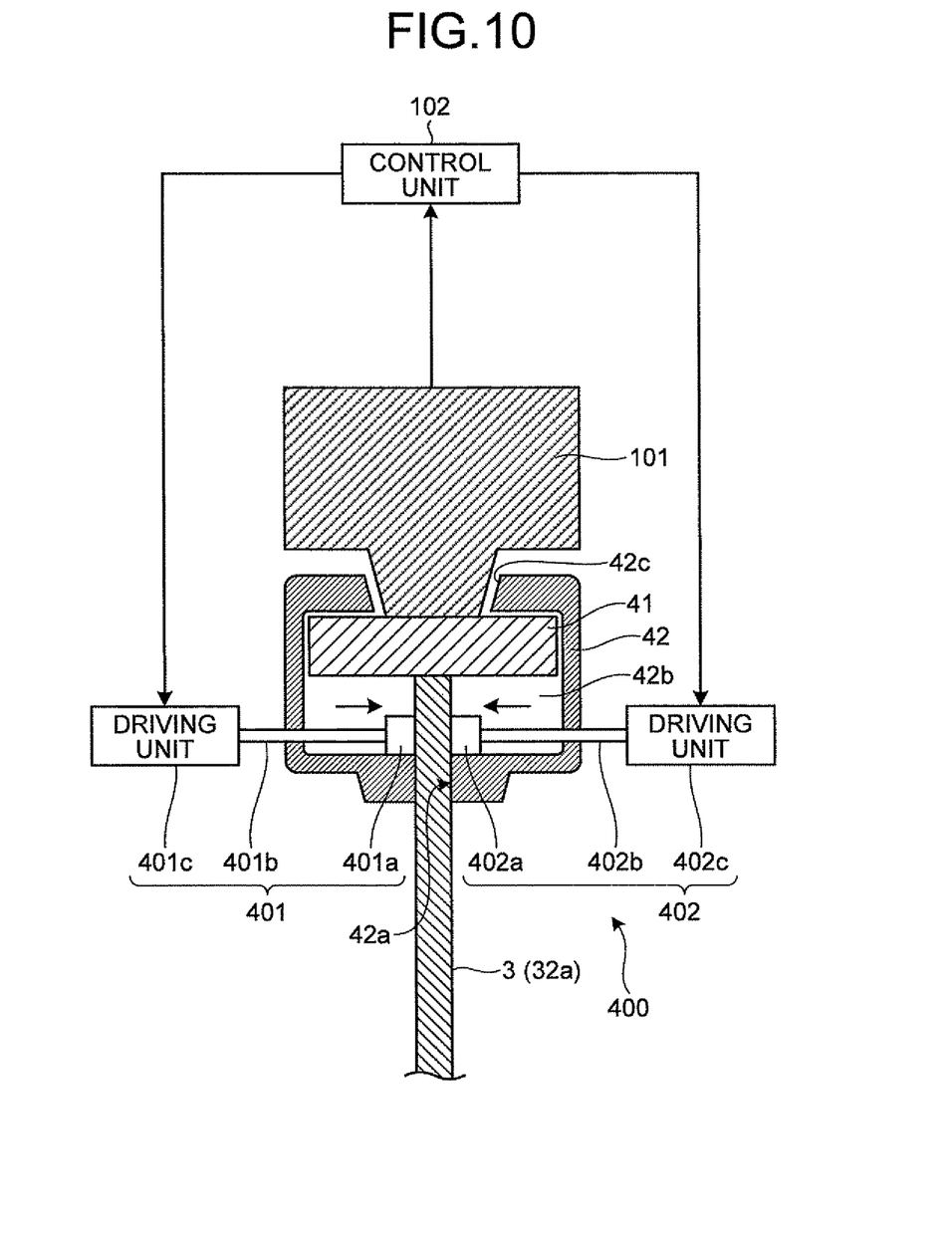
FIG. 10 is a cross-sectional view schematically illustrating a cross section of a calibration module according to a fifth embodiment of the invention.

Next, a fifth embodiment of the invention will be described. FIG. 10 is a cross-sectional view schematically illustrating a cross section of a calibration module according to the fifth embodiment. In FIG. 10, like reference numerals denotes like elements as in the configurations of the optical measurement system 1 and the calibration module 4 described above in conjunction with the first embodiment, and description thereof will not be repeated.

As illustrated in FIG. 10, a calibration module 400 includes two holding portions 401 and 402. The holding portion 401 includes a piston portion 401b forwardly and backwardly movable in a direction perpendicular to the insertion direction of the measurement probe 3, an elastic member 401a installed in the leading end of the piston portion 401b in contact with the side face of the leading end portion 32a of the measurement probe 3, and a driving unit 401c for driving the piston portion 401b. The other holding portion 402 has a configuration similar to that of the holding portion 401 and includes an elastic member 402a, a piston portion 402b, and a driving unit 402c. The holding portions 401 and 402 are arranged horizontally symmetrically to each other.

An outline of the operation of the calibration module 400 having the aforementioned configuration will be described. First, when the detection unit 101 detects insertion of the measurement probe 3, the control unit 102 causes the piston portions 401b and 402b to move forwardly toward the measurement probe 3 by driving the driving units 401c and 402c until they make contact with the measurement probe 3. As a result, the leading end portion 32a of the measurement probe 3 is interposed between the elastic members 401a and 402a.

Then, after the calibration process of the optical measurement system 1 is terminated, the control unit 102 causes each of the piston portions 401b and 402b to retreat from the measurement probe 3 by driving the driving units 401c and 402c. As a result, the leading end portion 32a of the measurement probe 3 is released from interposition between the elastic members 401a and 402a.

According to the fifth embodiment described above, the holding portions 401 and 402 are provided in the calibration module 400 so that it is possible to prevent the measurement probe 3 from getting out of the calibration module 400 until a user terminates the calibration process of the optical measurement system 1. Therefore, it is possible to reliably execute the calibration process before the measurement of the measurement target is performed.

Although the holding portions 401 and 402 are provided in the calibration module 400 in the fifth embodiment, for example, a plurality of holding portions may be provided in the calibration module 400.

Other Embodiments

Although a single spectroscope unit 24 is provided according to the first to fifth embodiments described above, a plurality of spectroscope units may be provided depending on the number of detection optical fibers provided in the measurement probe 3.

Although the spectroscope unit 24 is provided according to the first to fifth embodiment described above, for example, a photo sensor may be provided in the light source unit 22, and the photo sensor may be used to spectroscope the detection light incident through the measurement probe 3 or measure the detection light for each different wavelength range.

Although the irradiation of the illumination light and the detection of the detection light are performed using a single measurement probe in the first to fifth embodiments described above, for example, an irradiation probe for emitting the illumination light and a detection probe for detecting the detection light may be provided separately.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical measurement apparatus to which a base end portion of a measurement probe introduced into a subject is connected so that scattering light from the subject through the measurement probe can be measured, the optical measurement apparatus comprising:
a calibration member serving as an irradiation target of illumination light when a calibration process is performed for the measurement probe using the illumination light from the measurement probe;
an insertion portion where a leading end of the measurement probe can be inserted;
a housing portion that communicates with the insertion portion and accommodates the calibration member movably inside the housing portion along a penetration direction of the insertion portion;
a detection unit that detects a position of the calibration member inside the housing portion and detects insertion of the measurement probe when the detected position of the calibration member is a predetermined position in the housing portion; and
a control unit that performs control for initiating the calibration process when the detection unit detects the insertion of the measurement probe.

2. The optical measurement apparatus according to claim 1, wherein the detection unit comprises a switch unit that activates a power supply of the optical measurement apparatus in response to a manipulation force externally added, and
the power supply of the optical measurement apparatus is activated when the calibration member reaches a predetermined position in the housing portion and a manipulation force is added to the switch unit.

3. The optical measurement apparatus according to claim 2, further comprising a holding portion for holding the measurement probe,
wherein the control unit release holding of the measurement probe in the holding portion when the calibration process is terminated.

4. An optical measurement system comprising:
the optical measurement apparatus according to claim 1; and
the measurement probe detachably installed in the optical measurement apparatus.

5. The optical measurement apparatus according to claim 1, wherein the detection unit detects insertion of the measurement probe when the calibration member reaches a predetermined position in the housing portion to be in contact.

6. The optical measurement apparatus according to claim 5, further comprising a holding portion for holding the measurement probe,
wherein the control unit release holding of the measurement probe in the holding portion when the calibration process is terminated.

7. An optical measurement system comprising:
the optical measurement apparatus according to claim 5; and
the measurement probe detachably installed in the optical measurement apparatus.

* * * * *